United States Patent [19]

Dick

[11] Patent Number: 4,710,383

[45] Date of Patent: Dec. 1, 1987

[54] PHARMACEUTICAL DERMAL COMPOSITIONS WITH PROLONGED AND CONTINUOUS ACTION BASED ON ESSENTIAL FATTY ACIDS

[76] Inventor: P. R. Dick, 95 avenue de la Lanterne, 06000 Nice, France

[21] Appl. No.: 511,941

[22] Filed: Jul. 8, 1983

[30] Foreign Application Priority Data

Jun. 29, 1983 [FR] France .................................. 83 10735

[51] Int. Cl.$^4$ ...................... A61L 15/03; A61F 13/00; A61K 9/70
[52] U.S. Cl. .................................... 424/449; 604/896; 604/897
[58] Field of Search ...................... 424/312, 28, 16, 28, 424/449; 514/552; 604/896, 897

[56] References Cited

U.S. PATENT DOCUMENTS 4,150,109 4/1979 Dick et al. ............................ 424/28
4,543,247 9/1985 von Bittera et al. .................. 424/14
4,544,547 10/1985 von Bittera et al. .................. 424/14

FOREIGN PATENT DOCUMENTS 1594628 8/1981 United Kingdom .

OTHER PUBLICATIONS

Hoelgaard et al, Permeation of Linoleic Acid through Skin in Vitro, J. Pharm. Pharmocol., 34:610–611 (1982).

Primary Examiner—Shep K. Rose
Attorney, Agent, or Firm—Oblon, Fisher, Spivak, McClelland & Maier

[57] ABSTRACT

The present invention relates to novel dermal pharmaceutical compositions based on essential fatty acids. These compositions contain:
essential fatty acid (E.F.A.)—5 to 35% of the total weight—on a suitable solid macromolecular support;
diffusion regulators for the active components;
stabilizers of the plastics materials serving as a support, and
stabilizers for the E.F.A.'s. The invention is useful for the administration of medicaments to achieve a prolonged and continuous action.

18 Claims, No Drawings

PHARMACEUTICAL DERMAL COMPOSITIONS WITH PROLONGED AND CONTINUOUS ACTION BASED ON ESSENTIAL FATTY ACIDS

BACKGROUND OF THE INVENTION

The present inention relates to novel pharmaceutical compositions based on essential fatty acids (E.F.A.), for dermal use which exhibit prolonged and continuous action.

It is now universally acceptable, particularly since the work of BURR [J. Biol. Chem. 82 p. 342-345 (1929)] that the E.F.A.'s are indispensible for the animal kingdom and that their deficiency is involved in the appearance of dermatological lesions in man and in the animal. Immature or severed rats which are subjected to a lipidless diet exhibit poor growth, a squamous skin, a loss of fur and premature death. In other words, the rats show pathological picture as a result of a lipidless diet. The addition of E.F.A.'s and particularly the addition of linoleic and arachidonic acid to their diet prevents these symptoms. On the other hand, the addition of saturated and mono-unsaturated fatty acids has no effect.

In the dog, the deficiency results in the appearance of a cutaneous dryness and a slight depilation. Then, it is manifested by a desquamation and an exzema which gradually becomes generalised from the abdomen.

At present it is accepted that linoleic acid takes part as a structural element in the membranal phospholipids of the cells. It occurs in a form esterified at the $\beta$ position on the glycerol portion of these compounds. The presence of linoleic acid plays an important role in the integrity of the skin barrier. It avoids transepidermal loss of moisture.

The role of arachidonic acid and of homo $\gamma$ linoleic acid is quite different. These molecules come into action as prostaglandin precursors:

arachidonic acid (20:4 w 6) is the precursor of all prostaglandins with two double bonds;

homo $\gamma$ linoleic acid (20:3 w 6) is the precursor of all prostaglandins with one double bond.

The animal organism is not capable of synthesising these E.F.A.'s. In fact, dehydrogenases capable of creating a new double bond at w 6 or at w 3 do not exist in the animal world (they do, however, exist, in vegetables).

This enzymatic lack which is limited to a single biochemical step, prevents the synthesis of polyunsaturated E.F.A's of the two series w 6 and w 3. In addition, it prevents, from w 3 E.F.A.'s, the synthesis of w 6 E.F.A.'s and vice versa.

It is necessary to supply w 3 and w 6 E.F.A.'s at the same time to the animal. In mammals, it is particularly the w 6 E.F.A.'s which are important.

This synthetic defect and the biological importance of these molecules oblige the animal to find in its environment, sources of E.F.A.'s.

Two entry routes for these compounds into the organism exist: the digestive tract and the skin. It was BUTCHER (Journ. of Investig. Dermatology 16/1/1973 p. 43-48) who showed that linoleic acid passes rapidly through the skin barrier, penetrates into the cells of the epidermis and reaches the cutaneous capillaries. However after several years of treatment and tens of thousands of applications, practioners have observed that the local application of high doses of E.F.A.'s is contraindicated, because it results very frequently in an appreciable increase in the growth of the cells of the dermis.

It is the objective of the present invention to avoid this very troublesome drawback. It is also an objective of the present invention to provide a novel pharmaceutical preparation with prolonged and regulated action over time which is superior to other preparations containing E.F.A.'s, such as ointments, creams and lotions. It should also be appreciated that pharmacological and clinical advantages are realized by the continuous release of active substances for a prolonged period of the pharmaceutical preparations of the present invention.

GENERAL DESCRIPTION OF THE INVENTION

According to the present invention there is provided a novel solid pharmaceutical composition for dermal use, characterised in that it contains:

essential fatty acids (E.F.A.)—5 to 35% of the total weight—on a suitable solid macromolecular support;
diffusion regulators or the active components;
stabilisers for the plastics material serving as the support, and
E.F.A. stablising agents.

According to an advantageous embodiment of the invention, the solid macromolecular support is a thermoplastic support material containing plasticisers which confers flexibility and mechanical strength to the support material.

According to a particular feature of this embodiment, the thermoplastic support is a material selected from the group comprising polyethylene, polypropylene, ethylene and propylene copolymers, polyacrylates, vinyl polymers, vinyl halogenides, polyvinyl acetates, polyvinylidene type polymers, polyurethanes and polyaldehydes. The plasticisers are selected from the group comprising phosphoric acid esters, particularly tricresyl phosphate, phthalicacid esters, particularly methyl, ethyl, butyl, octyl or 2-ethyl hexyl phtalate, adipic acid esters, particularly ethyl, butyl, octyl or 2-ethyl hexyl adipate, azelaic acid esters, sebacic acid esters and maleic acid esters.

According to another embodiment of the invention, the E.F.A.'s are in the form of a pure product composed of:

| | |
|---|---|
| linoleic acid | (18:2 W 6) |
| and/or $\gamma$ linoleic acid | (18:3 W 6) |
| and/or arachidonic acid | (20:4 W 6) |
| and/or homo $\gamma$ linoleic acid | (20:3 W 6) |
| and/or linoleic acid | (18:3 W 3)) |
| and/or eicosapentaenoic acid | (20:5 W 3) |
| and/or docosahexaenoic acid | (22:6 W 3) |

According to another embodiment of the invention, the E.F.A.'s are added in the form of a naturally occurring oil of animal or vegetable origin.

According to another embodiment of the invention, the E.F.A.'s are included in the form of their esters, e.g., methyl and/or ethyl and/or propyl and/or isopropyl and/or butyl, which may be linear or branched.

According to another embodiment of the invention, the diffusion regulator of the active components, which function by modifying the porosity of the plastic matrix, are selected from the group comprising nitrogenous compounds, particularly benzenesulfonylhydrazine and trihydrazinotriazine, azo compounds, and particularly azodiisobutyronitrile, diaminobenzene or the azodicarbonamides.

According to another embodiment of the invention, the stabilisers for the plastic support materials are selected from the group comprising Ca stearate, Zn oxide, Ba oxide, Cd oxide and metallic complexes.

According to a particularly advantageous embodiment of the invention, the E.F.A. stabilisers are antioxidants selected from the group comprising alpha tocopherol and its esters, phenol or its aromatic derivatives, particularly butylhydroxyanisole, butylhydroxytoluene and polyphenols, particularly propyl, butyl or octyl gallates.

In accordance with the practices of the present invention, the active compounds of the invention may be administered alone or in combination with each other or administered in admixture with pharmaceutical additives such as inorganic fillers, dyes, pigments, deodorizers and the like.

According to the invention, the solid support is of the "sponge" or "blotting paper" type impregnated with E.F.A. introduced into a plastics material envelope of which the portion in contact with the skin perforated with by micropores.

Also in accordance with the invention, the solid support is in the form of a platelet of cardboard or of absorbant blotting paper, impregnated with the E.F.A. and stuck to a strip of plastics material with a suitable closure system.

It is also an object of the present invention to provide devices containing the compositions according to the present invention, which devices are characterised in that they are constituted by strips and/or bracelets and-/or bands and/or pastilles and/or rings provided with fastening or self-adhesive systems.

The invention is directed more particularly to the dermal pharmaceutical compositions based on an E.F.A. as well as devices comprising these compositions enabling the continuous and regulated release of these active substances which can be used both for man and animal in order to pevent and/or to cure various dermatological manifestations and general disorders associated with a deficiency of essential fatty acids in the organism.

These and other features of the invention will become clear to those skilled in the art upon the reading and understanding of the specification as well as the illustrative preferred embodiments which follow.

DESCRIPTION OF PREFERRED EMBODIMENTS

The invention will be better understood by means of the further description which follows, which refers to examples of the composition, examples of the manufacture and a report on gradual elimination tests of the active components.

It must however be well understood that these examples and report are given purely by way of illustration of the invention of which they do not constitute in any way a limitation thereof.

| EXAMPLES OF COMPOSITIONS | |
|---|---|
| | Parts by weight |
| Example 1 | |
| Methyl γ-linoleate | 18 |
| 2-ethyl hexyl adipate | 20 |
| Expoxidised soybean oil | 5 |
| Calcium stearate | 3 |
| Black iron oxide | 0.5 |
| Micronised silica | 1.5 |
| Butadiene-acrylonitrile copolymer | 5 |
| Vinyl chloride homopolymer | 47 |
| Example 2 | |
| Ethyl eicosapentaenoate | 15 |
| 2-ethyl hexyl adipate | 20 |
| Cadmium/barium/zinc complex | 1 |
| Calcium stearate | 3 |
| Black iron oxide | 0.3 |
| Red iron oxide | 0.2 |
| Micronised silica | 1 |
| Alpha tocopherol | 1.5 |
| Vinyl chloride homopolymer | 58 |
| Example 3 | |
| Ethyl arachidonate | 10 |
| Ethyl γ-linoleate | 5 |
| Ethyl linoleate | 5 |
| 2-ethyl hexyl adipate | 18 |
| Expoxidised soybean oil | 4 |
| Butylhydroxyanisole | 0.1 |
| Butylhydroxytoluene | 0.1 |
| Yellow iron oxide | 0.3 |
| Titanium dioxide | 0.5 |
| Calcium stearate | 5 |
| Butadiene acrylonitrile copolymer | 8 |
| P.V.C. homopolymer | 44 |
| Example 4 | |
| Cod liver oil | 25 |
| Butyl adipate | 15 |
| Alpha tocopherol | 5 |
| Calcium stearate | 5 |
| Butadiene acrylonitrile copolymer | 10 |
| Calcium carbonate | 8 |
| Titanium dioxide | 1 |
| P.V.C. homopolymer | 31 |
| Example 5 | |
| Methyl homo γ linoleate | 10 |
| Ethyl eicosapentaenoate | 5 |
| Ethyl docosahexaenoate | 5 |
| 2-ethyl hexyl phtalate | 12.5 |
| Calcium stearate | 5 |
| Aluminium magnesium silicate | 6 |
| Yellow iron oxide | 0.5 |
| Alpha tocopherol | 1 |
| P.V.C. homopolymer | 5 |
| Example 6 | |
| Esterified linseed oil distillate | 15 |
| 2-ethyl hexyl adipate | 20 |
| Calcium stearate | 5 |
| Calcium carbonate | 5 |
| Black iron oxide | 0.5 |
| Octyl gallate | 0.5 |
| Butadiene-acrylonitrile copolymer | 4 |
| P.V.C. homopolymer | 49 |

EXAMPLE 7

The general hot extrusion method is used. The substances are those of Example 2.

Into a suitable mixer equiped with a double wall heating system, are introduced 38 kg of P.V.C. homopolymer, 20 kg of 2-ethyl hexyl adipate, 1 kg of cadmium/-barium/zinc complex, 3 kg of calcium stearate, 0.3 kg of black iron oxide, 0.2 kg of red iron oxide.

The mixture is stirred for 30 min. while heating the powder to 80°–85° C. and then allowing the mixture to cool with stirring. When the mass is at about 30° C., there are introduced in order: 1.5 kg of alpha tocopherol, 1 kg of micronised silica, 20 kg of P.V.C. polymer and 15 kg of ethyl eicosapentaenoate. The mixture is stirred for about 15 minutes.

The powder obtained which is a uniform brown colour, is immediately introduced into the supply hopper of a screw extruder. At the outlet of the die the strip obtained is cooled by immersion in a tank of cold awater then cut automatically to the desired length.

The extrusion parameters: temperature of the dye, speed and pressure of extrusion, are fixed so as to obtain a strip of uniform appearance and size. The cross-section of the strip is fixed by the dimensions of the die and are, by way of example, 10 mm wide by 3 mm thickness. The plastic strip is heat-welded to a P.V.C. strip of 14 mm width and having at its ends a self-adhesive type fastening system.

The final device is rolled and packaged in welded sachets with three thicknesses (P.V.C.-aluminium-paper). The dimensions of the device permit its fastening either to the wrist or to the ankle in man.

EXAMPLE 8

The general method of hot-moulding is used. The substances are those of Example 5.

At 70° C. the following are mixed intimately, 12.5 kg of 2-ethyl hexyl phthalate, 5 kg of calcium stearate 6 kg of aluminium and magnesium silicate, 0.5 kg of yellow iron oxide and 55 kg of P.V.C. homopolymer.

After 30 minutes, the powder is left to cool to ambient temperature and there are added with stirring: 1 kg of alpha tocopherol, 10 kg of methyl homo γ-linoleate, 5 kg of ethyl eicosapentaenoate, 5 kg of ethyl docosahexaenoate.

The mixture which is, yellow in colour, is then hot formed in moulds enabling the production of oval pellets of 2 mm thickness, 15 mm small diameter and 30 mm large diameter.

They are fixed by sticking the pellets to an adhesive tape and packaged in welded sachets.

EXAMPLE 9

The strips obtained in Example 7 are cut to length of 60 cm and provided with a loop riveted to one of its ends.

They may be fixed to the neck of domestic animals (dog or cat).

REPORT OF ELIMINATION TESTS

The devices obtained in Example 7 are fixed to the ankles of 20 volonteer persons and worn for 10 consecutive weeks.

A tolerance examination showed that in this period, no sign of irritation or of allergy was detected in each of the subjects. In addition, no excessive sweating from the plastic web was observed.

Elimination checks were carried out each week and were based on the analysis of two of the above tester devices.

The active substance: ethyl eicosapentaenoate remaining in the P.V.C. matrix was analysed according to the following procedure:
dissolution by tetrahydrofuran of 1 g of strip.
precipitation of the polyvinyl chloride by hexane.
after filtration, the organic eluate containing both ethyl eicosapentaenoate and the plasticiser (2-ethyl hexyl adipate) is analysed by aqueous phase chromatography.

The qualitative and quantitative determination was carried out by comparison of the retention times and of the areas of the peaks detected with respect to a control solution.

The table below groups the values bearing on the amounts remaining of ethyl eicosapentaenoate expressed per gram of active strip ($R_{mg}$) as well as the content in mg calculated eliminated per day ($T_{mg}$) and per gram of plastics material.

TABLE I

| Week | 0 | 1 | 2 | 3 | 4 | 5 | 6 | 7 | 8 | 9 | 10 |
|---|---|---|---|---|---|---|---|---|---|---|---|
| $R_{mg}^{m}$+ | 152 | 141 | 125 | 103 | 85 | 67 | 51 | 40 | 29 | 18 | 10.5 |
| $T_{mg}$+ | — | 1.57 | 2.28 | 3.14 | 2.57 | 2.57 | 2.28 | 1.57 | 1.57 | 1.57 | 1.07 |

+The initial amount (time T = 0) of ethyl eicosapentaenoate was 152 mg per g of plastics material While the invention has been described and illustrated with reference to certain preferred embodiments thereof, those skilled in the art will appreciate that various changes, modifications, and substitutions can be made therein without departure from the spirit of the invention. It is intended, therefore, that the invention be limited only by the scope of the claims which follow.

I claim:

1. In a transdermal delivery device for providing continuous and regulated release of essential fatty acids to a mammal, to prevent disorders associated with a deficiency in essential fatty acids, the improvement comprising incorporating therein from 5 to 35% of the total weight of an active component which is selected from the group consisting of linoleic acid (18:2ω6), γ-linolenic acid (18:3ω6), arachidonic acid (20:4ω6), γ-homo-linolenic acid (20:3ω6), linoleic acid (18:3ω3), eichosapentaenoic acid (20:5ω3), docosahexaenoic acid (22:6ω3), their linear and branched $C_{1-4}$ esters, and mixtures thereof, diffusion regulators for said active component selected from the group consisting of nitrogenous compounds and azo compounds, and stabilizing agents for said active component comprising anti-oxidants selected from the group consisting of alpha tocopherol and its esters, phenol and its aromatic derivatives, polyphenols and propyl, butyl or octyl gallates.

2. The device of claim 1, wherein said transdermal delivery device comprises:
   (a) a pharmaceutically suitable solid macromolcular thermoplastic support for said active component;
   (b) stabilizers for said macromolecular thermoplastic support; and
   (c) plasticizers for said macromolecular thermoplastic support conferring flexibility and mechanical strength.

3. The device of claim 2, wherein the said macromolecular thermoplastic support is of a material selected from the group consisting of polyethylene, polypropylene, copolymers of ethylene and propylene, polyacrylates, vinyl polymer, vinyl halogenpolymers, polyvinyl acetals, polymers of the polyvinylidene type, polyurethanes and polyaldehydes; and the plasticizers are selected from the group consisting of phosphoric acid esters, phthalic acid esters, adipic acid esters, azelaic acid esters, sebacic acid esters and maleic acid esters.

4. The device of claim 2, wherein the said active component is in the form of a naturally occurring oil of animal or vegetable origin.

5. The device of claim 2, wherein the said stabilizers are selected from the group consisting of Ca stearate, Zn oxide, Ba oxide, Cd oxide and metal complexes thereof.

6. The device of claim 2, further comprising a pharmaceutical additive which is at least one member selected from the group consisting of inorganic fillers, dyes, pigments and deodorizers.

7. The device of claim 2, manufactured by a hot extrusion method.

8. The device of claim 2, having the form of a strip, a bracelet, a pastille or a ring provided with a fastening or a self-adhesive system.

9. The device of claim 3, wherein:
the said phosphoric acid ester is tricresyl phosphate;
the said phthalic acid esters are methyl, ethyl, butyl, octyl or 2-ethylhexylphthalate; and
the said adipic acid esters are ethyl, butyl, octyl or 2-ethylhexyl adipate.

10. The device of claim 1, wherein:
the said nitrogenous compounds are benzenesulfonylhydrazine or trihydrazinotriazine; and
the said azo compounds are azodiisobutyronitrile, diaminobenzene or a azodicarbonamide.

11. The device of claim 1, wherein:
the said aromatic derivatives are butylhydroxyanisole or butylhydroxytoluene.

12. A method for providing continuous and regulated release of essential fatty acids to a mammal, to prevent disorders associated with a deficiency in essential fatty acids, comprising placing onto the skin of a mammal in need thereof a transdermal delivery device incorporating therein from 5 to 35% of the total weight of an active component which is selected from the group consisting of linoleic acid (18:2ω6), γ-linolenic acid (18:3ω6), arachidonic acid (20:4ω6), γ-homo-linolenic acid (20:3ω6), linolenic acid (18:3ω3), eichosapentaenoic acid (20:5ω3), docosahexaenoic acid (22:6ω3), their linear and branched $C_1$-$C_4$ esters, and mixtures thereof, diffusion regulators for said active component selected from the group consisting of nitrogenous compounds and azo compounds, and stabilizing agents for said active component comprising anti-oxidants selected from the group consisting of alpha tocopherol and its esters, phenol and its aromatic derivatives, polyphenols and propyl, butyl or octyl gallates.

13. The method of claim 12, wherein said transdermal delivery device comprises:
(a) a pharmaceutically suitable solid macromolecular thermoplastic support for said active component;
(b) stabilizers for said macromolecular thermoplastic support; and
(c) plasticizers for said macromolecular thermoplastic support conferring flexibility and mechanical strength.

14. The method according to claim 13, wherein the said device is placed on the skin of the mammal for as long a period of time as ten weeks.

15. The method according to claim 13, wherein said device comprises an envelope of plastic material, a portion of which in contact with the skin is perforated with micropores.

16. The method according to claim 13, wherein the said device comprises a strip of plastic material comprising a closure system thereof.

17. The method according to claim 13, wherein the said device is shaped as a plastic strip, a bracelet, a band, a plastille, a ring or combinations thereof, and is provided with a fastening or self-adhesive device to the skin.

18. The method of claim 13, wherein the said disorder is a skin disorder.

* * * * *